United States Patent [19]
Heck et al.

[11] Patent Number: 5,097,548
[45] Date of Patent: Mar. 24, 1992

[54] INFLATABLE SELF-SUPPORTING COVER

[76] Inventors: Douglas M. Heck, 1610 Weisel Rd., Quakertown, Pa. 18951; Robert W. Alexander, 103 Fenwick Rd., Cherry Hill, N.J. 08034

[21] Appl. No.: 510,574

[22] Filed: Apr. 18, 1990

[51] Int. Cl.⁵ .................... A47C 29/00; A47G 9/02
[52] U.S. Cl. .......................................... 5/414; 5/482
[58] Field of Search .................. 5/284, 421, 423, 414, 5/402; 4/535, 536; 62/261; 128/205.26, 400, 402; 52/2 J, 2 K

[56] References Cited

U.S. PATENT DOCUMENTS

| | | | |
|---|---|---|---|
| 771,847 | 10/1904 | Titus | 5/284 |
| 2,093,834 | 9/1937 | Gaugler | 5/423 X |
| 2,235,966 | 3/1941 | Summers | 62/261 X |
| 2,782,794 | 2/1957 | White | 52/2 J |
| 2,830,606 | 4/1958 | Daugherty | 52/2 J |
| 3,247,627 | 4/1966 | Bird | 5/2 J |
| 4,237,914 | 12/1980 | Gantz | 52/2 J |
| 4,572,188 | 2/1986 | Augustine et al. | 62/261 X |
| 4,660,388 | 4/1987 | Greene, Jr. | 62/261 |

Primary Examiner—Michael F. Trettel
Attorney, Agent, or Firm—Joseph J. OKeefe; Charles A. Wilkinson

[57] ABSTRACT

An inflatable, self-supporting cover suitable for placement over a body and comprising a top sheet, a bottom sheet and ribs extending between such sheets to form a plurality of compartments extending transverse to the length of the cover. The ribs are formed in the shape of a flattened oval and then fastened between such sheets. A duct extending longitudinally of the length of the cover connects with the compartments and with a source of pressurized air which inflates the compartments, causing them to assume an arch-like shape extending transverse to the length of the cover and spanning said body. An alternative embodiment includes a second cover section fastened to the cover bottom sheet and having a plurality of compartments, each with at least one port therein. The second cover section compartments connect with the duct whereby pressurized air passes to the second cover section compartments and from each port therein to circulate air about the body beneath the cover.

36 Claims, 6 Drawing Sheets

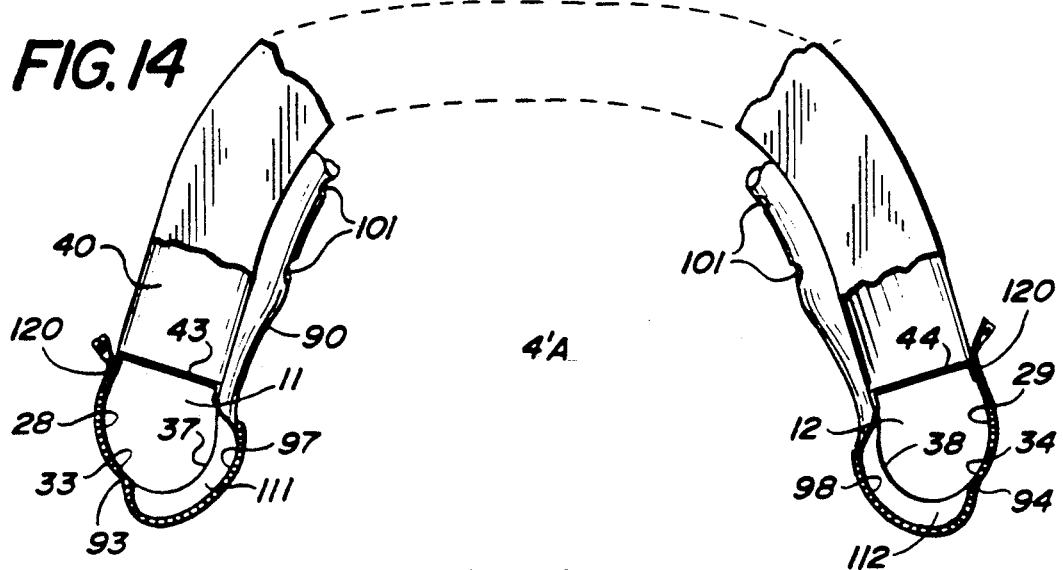
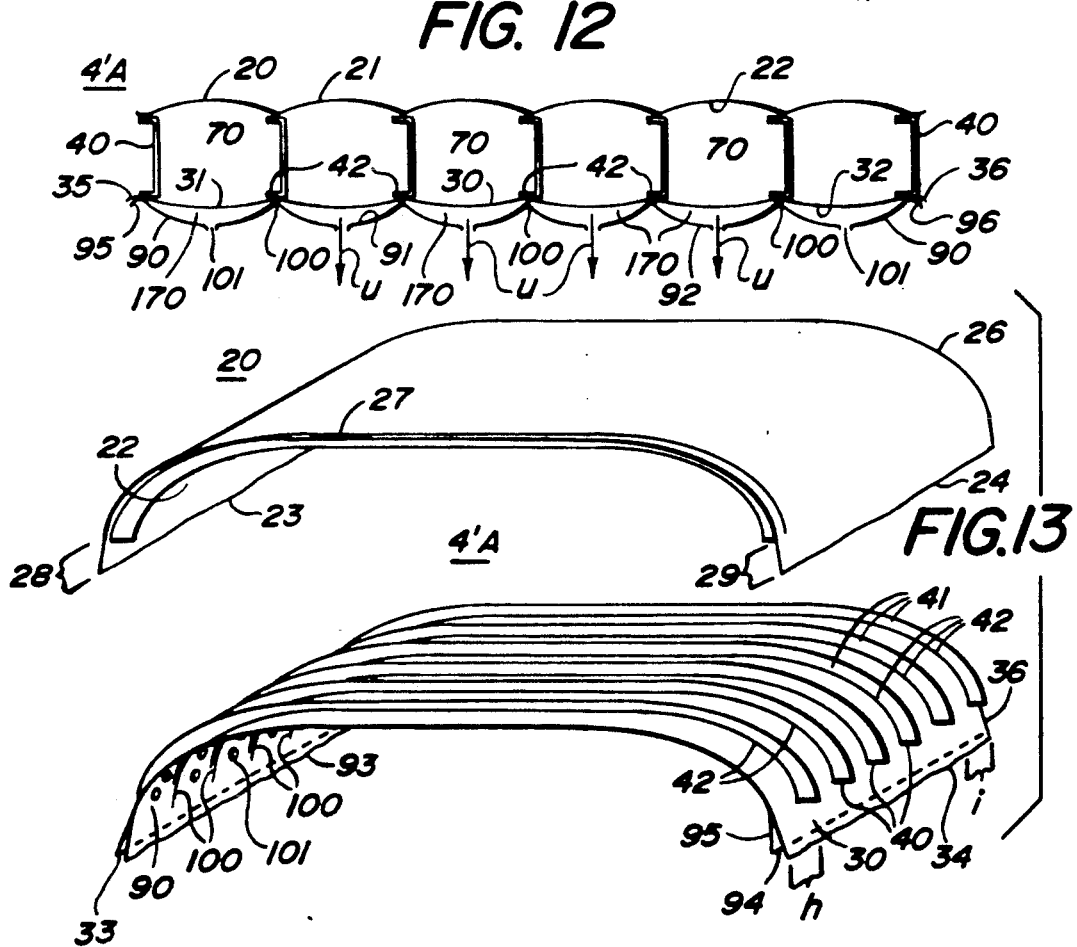

INFLATABLE SELF-SUPPORTING COVER

BACKGROUND OF THE INVENTION

This invention relates to an inflatable, self-supporting cover for the occupant of a bed. More particularly, this invention relates to an inflatable, self-supporting cover suitable for placement over the occupant of a bed and, when desirable, for treating such occupant by controlling the atmosphere beneath the cover.

The cover of this invention is particularly suitable in conjunction with the treatment of patients suffering from disorders or injuries affecting the skin and body heat regulation, as, for example, burn victims and neurological and post-operative patients. In treating such patients it is most desirable to avoid contacting a patient's skin with any type of material.

The skin of a human body functions as a shield by acting as a protective mechanism against temperature changes, providing insulation for external heat, serving as protection against dehydration and acting as a barrier against certain diseases. When a person loses skin, particularly due to burns, that person's body shield is lost, or at least damaged, and he or she faces unique medical problems and complications different from those of a typical injured person. The problems and complications created by burns require extra precautions and special treatment.

When a person is burned, a scale or eschar forms over the burn area and functions as a temporary shield until new skin has a chance to form. To treat a burn patient it is important to keep the eschar dry in order to decrease the probability of infection. It has been learned that warm, dry air circulated over a burn area will aid in the rapid formation of a dry eschar and will enhance evaporation of moisture from the eschar and reduce body heat loss.

In treating burn patients it is very important to minimize heat loss because as a burn patient's temperature drops, the body spends most of its energy generating heat rather than rebuilding damaged tissue and fighting disease. Current therapy options for regulating the body temperature of a burn patient include the use of ice packs or heating pads, as required, directly on the skin. Unfortunately, the direct contact of any object with the skin or eschar increases the possibility of infection.

By virtue of recognized problems associated with certain known procedures and equipment for treating burn patients, as well as for treating those with other medical problems, it has been recognized that there may be advantages in regulating a patient's body temperature and keeping the skin dry through convective procedures. In conjunction with such procedures it is important to closely monitor the temperature in the fluctuating heat environment of a burn patient's body.

Various types of structures have heretofore been available for covering and/or treating the environment surrounding a patient. U.S. Pat. No. 3,444,922 describes apparatus which includes at least one porous bed covering through which air is passed to circulate about the body of a patient beneath such covering. A major drawback of the apparatus is that the bed covering is in contact with the patient's skin.

U.S. Pat. No. 4,572,188 describes a self-supporting airflow cover for surrounding at least a portion of a patient's body. The cover comprises a plurality of parallel tubes which extend longitudinally of the patient's body and are interconnected along seams at their edges. Gas from a blower is delivered through a hose to an input port of a keystone tube and passes through transverse ports into all of the other tubes to cause them to inflate and provide the cover with what is stated to be a self-supporting structure having a generally rounded cross-sectional shape. The gas passes from the cover through a plurality of exit ports in the lower portion of all of the tubes to bathe the patient's body. This cover has several objectional features. The gas pressure causes certain tubes to elevate only slightly, if at all, above the patient so that any movement of the patient causes skin contact with the cover, gas circulation to the cover can not be interrupted without having the cover collapse, and the delivery hose must be supported independently above the cover, which interferes with treatment of the patient.

In some hospitals burn patients are shielded by a system of covers suspended from ropes and/or wires so as to be spaced from a patient's body. While such a system provides a cover that does not contact a patient's body, the system is cumbersome and complicates procedures for treating a patient beneath the cover.

Other supported shelters and air covers of a variety of types are well known. Possibly the most visible of such shelters are the air-supported, tent-like structures used for indoor athletic events, such as those that cover tennis courts. The peripheries of these structures are anchored at ground level to maintain an air-tight seal between the bottom of the structure and its base, and the tops or domes are maintained in position by pressurized air supplied by a compressor to the interior of the structure. U.S. Pat. No. 4,183,184 describes such a shelter system comprising an inflatable enclosure sealed along its bottom periphery and a blower for inflation thereof. Such shelters or covers are unsuitable for covering or treating patients.

The inventors of the inflatable self-supporting cover of this invention first considered variations of the above described apparatus and structures, but all of such variations created problems or offered no special benefits for the treatment of the occupant of a bed, such as a hospital patient.

OBJECTS OF THE INVENTION

Accordingly it is an object of this invention to provide a self-supporting, open-ended cover particularly useful for treatment of hospital patients and which, through the use of low-pressure air, will rest or sit above and out of contact with such patients without any requirement for external support.

It is another object of the invention to provide an air inflatable, self-supporting, open-ended cover for the occupant of a bed which is spaced from the bed occupant in a manner to permit his or her reasonable movement without contact with the cover and is lightweight, strong, portable and easily folded and stored.

It is another object of the invention to provide an air inflatable, self-supporting cover for the occupant of a bed which looks, performs and feels somewhat like a traditional blanket and is inherently safe to use and which may include several sections, any of which may be raised independently of the others in order to treat a particular area of a patient's body.

Another object of the invention is to provide an air inflatable, self-supporting cover capable of economical fabrication in a number of sizes to fit different size beds.

It is still another object of the invention to provide an air inflatable, self-supporting cover which includes a blower system that provides air both to support the cover and for circulation about a patient beneath the cover and which operates quietly so as to avoid annoyance to such patient and other patients in adjoining areas.

SUMMARY OF THE INVENTION

The objects of the invention are accomplished by providing an inflatable, self-supporting, open-ended cover for placement, independent of any external support, over a patient lying on a mattress on a bed. The cover extends longitudinally of the bed and patient and comprises a support portion and connecting air ducts at each end of the support portion. One or both such ducts are connected through a tube to a source of air, such as a low pressure blower or compressor. Air fed from the blower to an air duct and then to the cover support portion causes it to inflate into an arch-like shape, transversely of the bed, with a slightly curved upper, central portion and downwardly and outwardly extending, leg portions, in a manner to bridge the patient. There is adequate clearance between the underside of the cover and the top of the mattress to provide reasonable clearance for the patient to turn and move without contacting the cover.

The cover comprises a top sheet, a bottom sheet and a plurality of inner spaced ribs which extend transversely of the cover and divide the cover support portion into a plurality of elongated, adjacent compartments that extend transversely of the length of the cover, with an air duct at each end of the compartments. The cover top and bottom sheets have about the same length and width, the length extending longitudinally of the cover and the width transversely of the cover. Each of the rib pieces is cut from a single piece of material in the configuration or shape of a generally "flattened oval", as hereinafter defined. Each rib top, which is the outer periphery of the oval, has a length longer than that of the rib bottom, which is the inner periphery of the oval. The cover top sheet has a transverse width greater than the length of the top of each rib and opposite end portions of the top sheet extend beyond the ends of each rib. The cover bottom sheet has a transverse width greater than the length of the bottom of each rib and opposite end portions of the bottom sheet extend beyond the ends of each rib. Spaced from opposite ends of the ribs, the extending end portions of the top and bottom sheets are joined adjacent their edges to form the air ducts.

The generally flattened oval, as-cut shape of the ribs is forced to assume an arch-like shape as the ribs are fastened to the cover top and bottom sheets which in effect acts to prestress the cover top support portion. Thus, when air is fed into the cover top support portion compartments, they inflate and cause the top support portion to assume an arch-like shape, with downwardly and outwardly extending leg portions, which makes the cover self-supporting and provides adequate clearance between the underside of the cover and a patient resting beneath the cover on a bed.

In another embodiment of the invention, the cover is provided with a lower portion comprising a supplemental sheet, which is fastened along spaced seams to the underside of the cover bottom sheet to form a plurality of lower compartments which extend transversely of the cover. In the supplemental sheet and extending longitudinally of each such lower compartment are a plurality of ports. Like the cover, the lower portion has an air duct at each end of the lower compartments. One of the ducts is connected by an air tube to a source of pressurized air, such as a blower, which may be the same blower that inflates the cover. Pressurized air from the blower passes to the lower portion air duct, flows into the lower compartments and exits through the ports to circulate over a patient positioned beneath the cover. Apparatus may be provided between the cover lower portion air duct and its source of pressurized air to control the quality and temperature of the air circulated about a patient.

BRIEF DESCRIPTION OF THE DRAWINGS

The nature of the invention will be more clearly understood by reference to the following description, the appended claims and the several views illustrated in the accompanying drawings.

FIG. 12 is a sectional view taken along the line 12—12 of the embodiment of the cover section of the invention shown in FIG. 11.

FIG. 13 is a view showing the partial assembly of the parts of one section of the cover of the embodiment of the invention shown in FIGS. 11 and 12.

FIG. 14 is an enlarged fragmentary sectional view of the lower end portions of the embodiment of the cover section of the invention shown in FIGS. 11, 12 and 13.

DESCRIPTION OF THE PREFERRED EMBODIMENT

Figure 1:
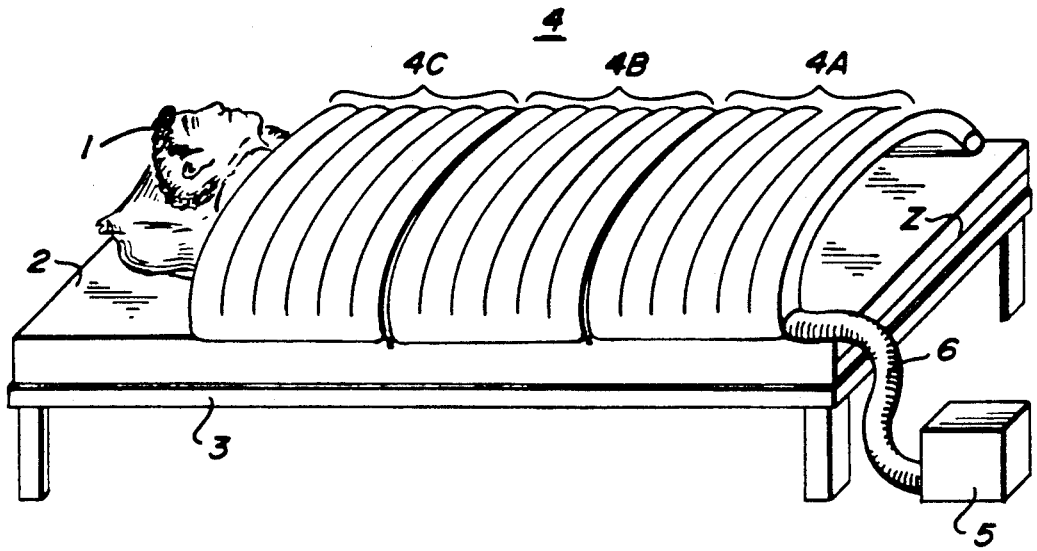
FIG. 1 is a perspective view of one embodiment of the invention showing the air-inflatable, self-supporting cover, which has three sections, positioned over a patient in a bed.
Figure 2:
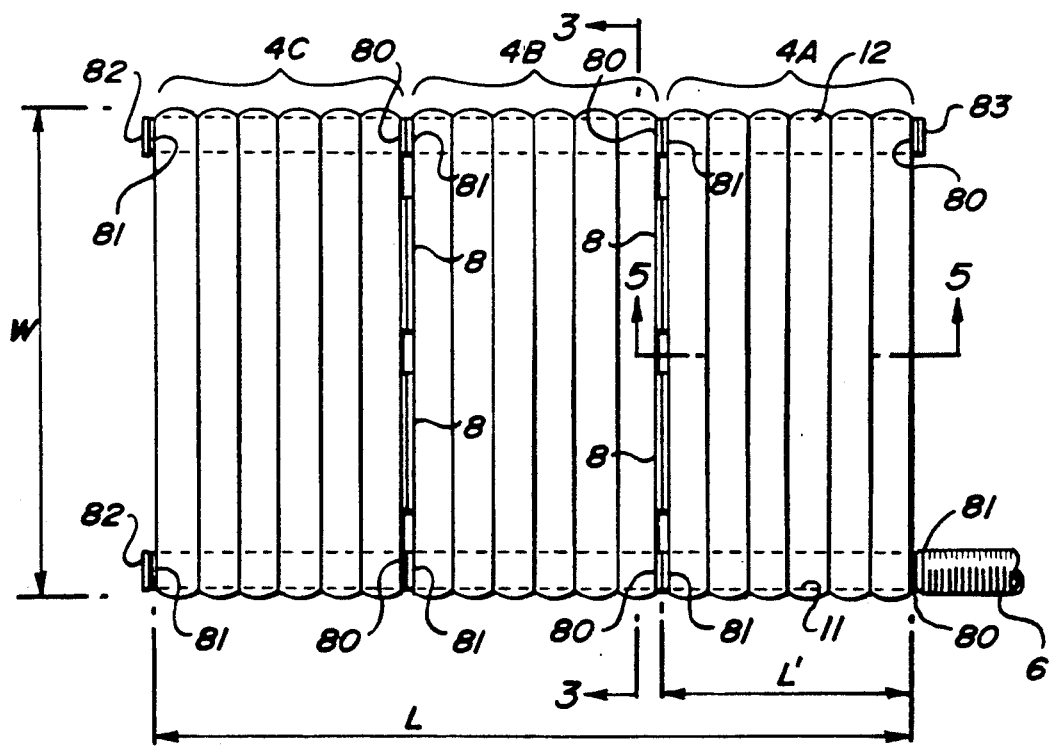
FIG. 2 is a top plan view of the cover of the invention shown in FIG. 1.

In FIG. 1 there is shown a patient 1 lying on mattress 2, which has a width Z, of hospital bed 3. Positioned above patient 1 is open-ended, self-supporting cover 4 having three sections 4A, 4B and 4C of similar construction. Cover 4 is inflated by pressurized air from blower 5 conducted through delivery tube 6 to cover section 4A and from there to sections 4B and 4C. Cover 4 extends longitudinally of mattress 2, and, as shown in FIG. 2, has a width W of about 34 inches and a length L of about 72 inches. Cover sections 4A, 4B and 4C each has a length L' of about 24 inches, ⅓ the length of cover 4 and the same width W as that of cover 4, and each extends transversely of mattress 2. Cover sections 4A, 4B and 4C are fastened together along their adjacent sides, unnumbered, by fasteners 8 of a type known to those skilled in the art, for example, by Velcro fasteners or by tabs and buttons.

Figure 3:
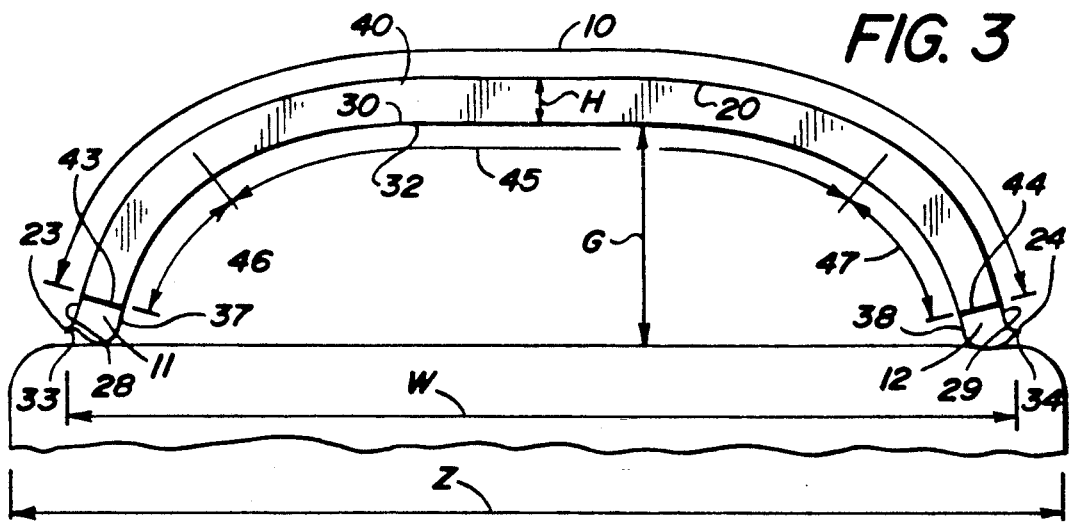
FIG. 3 is a sectional view of the cover taken along the line 3—3 of FIG. 2.
Figure 4:
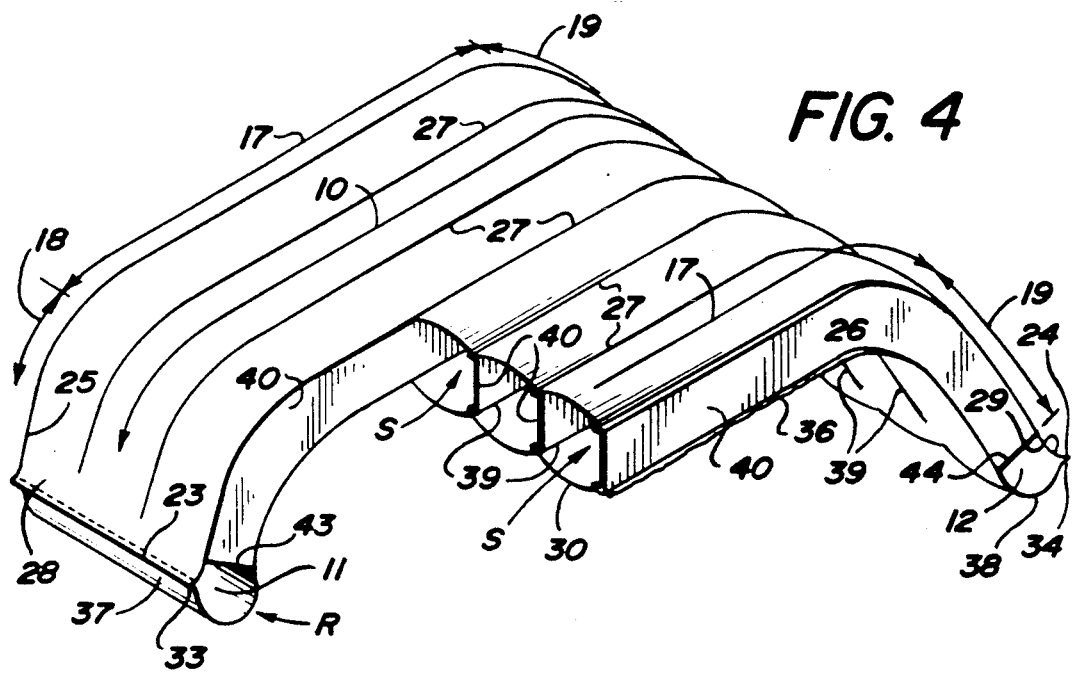
FIG. 4 is a perspective view, partly in section, illustrating one section of the cover shown in FIG. 1.

As best shown in FIGS. 3 and 4, cover section 4A comprises support portion 10 and air ducts 11 and 12, respectively, which extend transversely at opposite lower ends, unnumbered, of support portion 10. As best shown in FIGS. 3–6, support portion 10 comprises top sheet 20, bottom sheet 30 and seven spaced, generally parallel ribs 40, which divide cover section 4A into six adjacent, generally parallel compartments 70 that extend longitudinally of the width W of cover section 4A and transversely of the length L of cover 4. The width W of cover section 4A is slightly smaller than the width Z of mattress 2.

Figure 6:
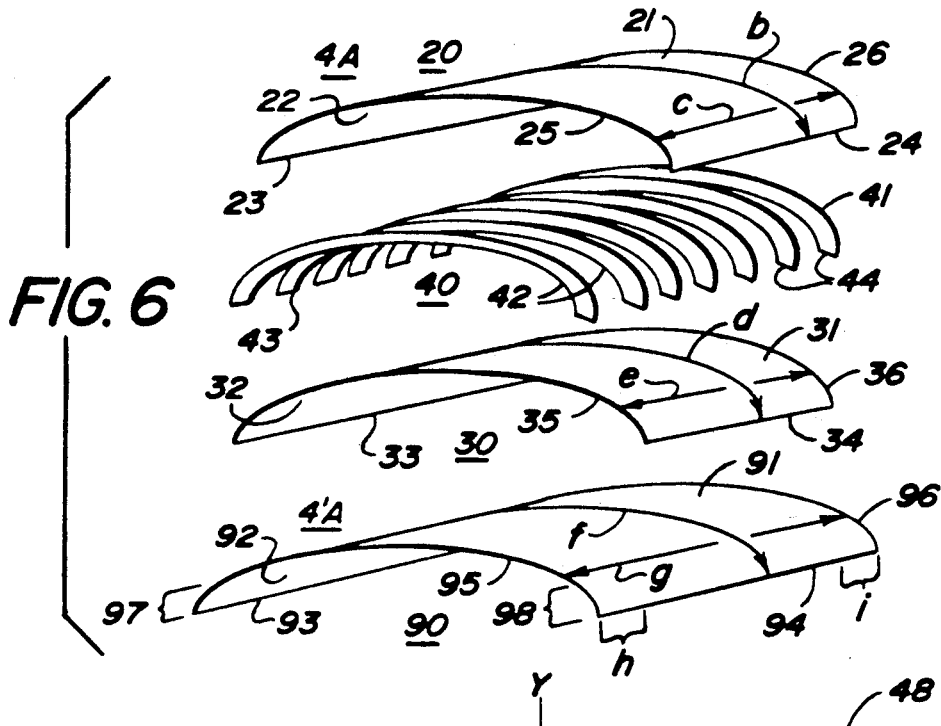
FIG. 6 is an exploded, schematic, perspective view of the parts of one section of the cover of this invention and one part of an alternative embodiment of the invention.

As best shown in FIG. 6, top sheet 20 of cover section 4A has top side 21, underside 22, front edge 23, central portion, unmarked, back edge 24 and sides 25 and 26. Top sheet 20 is rectangular in shape and has a length b of about 70 inches and width c of about 25 inches. Bottom sheet 30 has top side 31, underside 32, front edge 33, back edge 34 and central portion, unmarked, sides 35 and 36. Bottom sheet 30 is rectangular in shape and has a length d of about 70 inches and width e of about 25 inches, the same length and width as top sheet 20.

Figure 5:
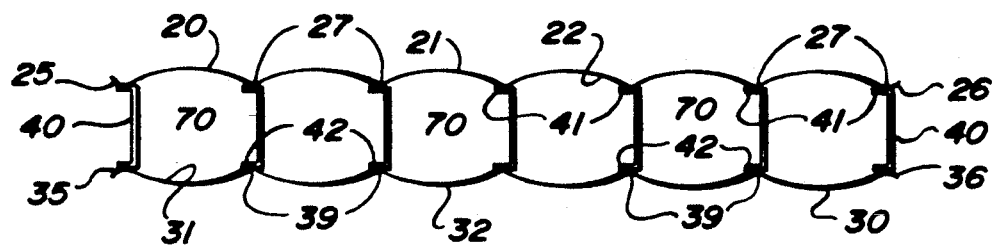
FIG. 5 is a sectional view taken along the line 5—5 of FIG. 2.

As shown schematically in FIGS. 3, 5 and 6, each rib 40 has a top 41, bottom 42, ends 43 and 44 and a height H of about 2 inches, which includes the small overlapping portions where the rib is joined to the top and bottom sheets. When cover section 4A is inflated, each rib 40 assumes an arch-like shape, for reasons hereinafter explained, having a slightly curved upper portion 45 and downwardly and outwardly extending, bowed leg portions 46 and 47, respectively.

Figure 7:
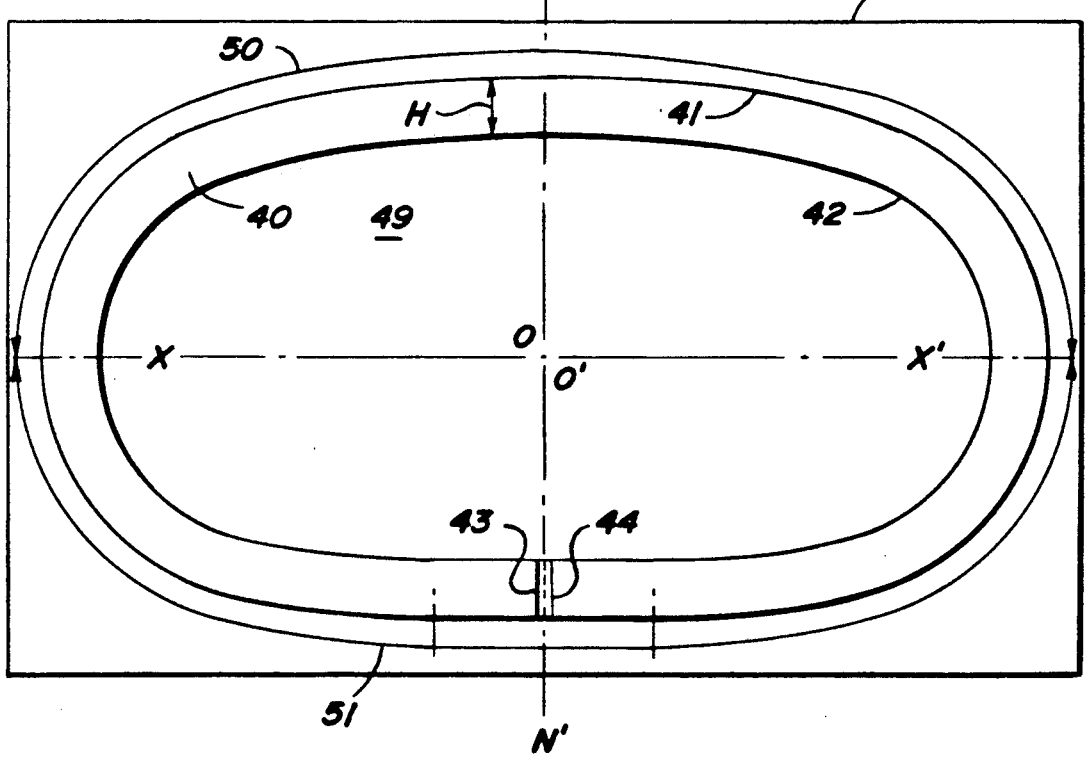
FIG. 7 is a view of the layout of one embodiment of the design of the rib portion of the cover of this invention.

One embodiment of rib 40 is laid out, as shown in FIG. 7, on a sheet of material 48 in a shape 49, which is referred to generally as "a flattened oval", hereinafter defined. Flattened oval 49 represents a composite figure laid out with the upper portion 50 in the shape of the top half of an ellipse 60, as shown in FIG. 8, and the lower portion 51 in the shape of the bottom half of a smaller ellipse 61 as shown in FIG. 9, which is elongated as hereinafter described.

Figure 8:
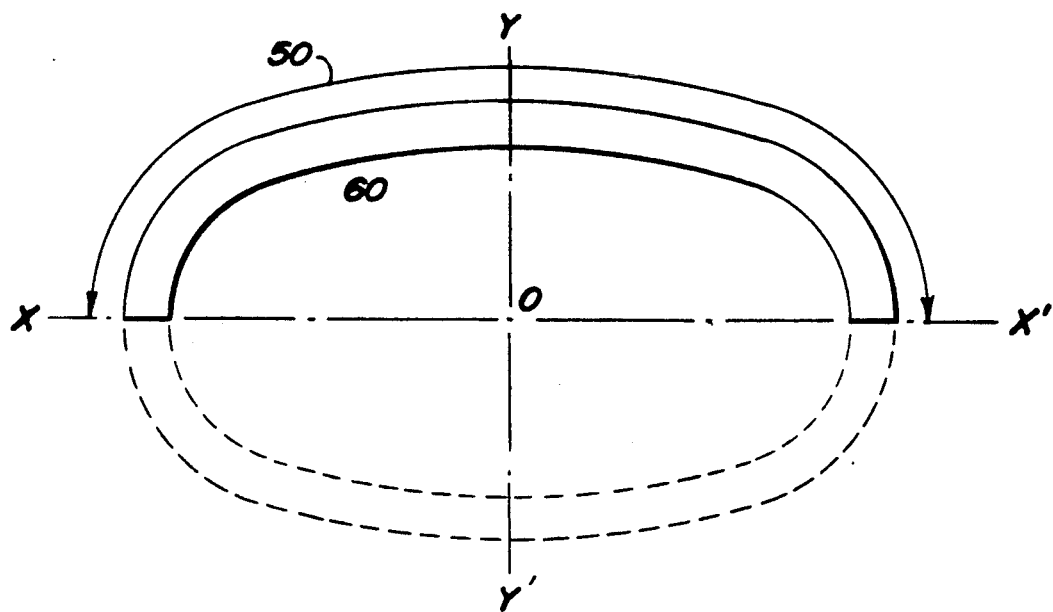
FIG. 8 is a view of the layout of the design of the upper portion of the rib of FIG. 7.
Figure 9:
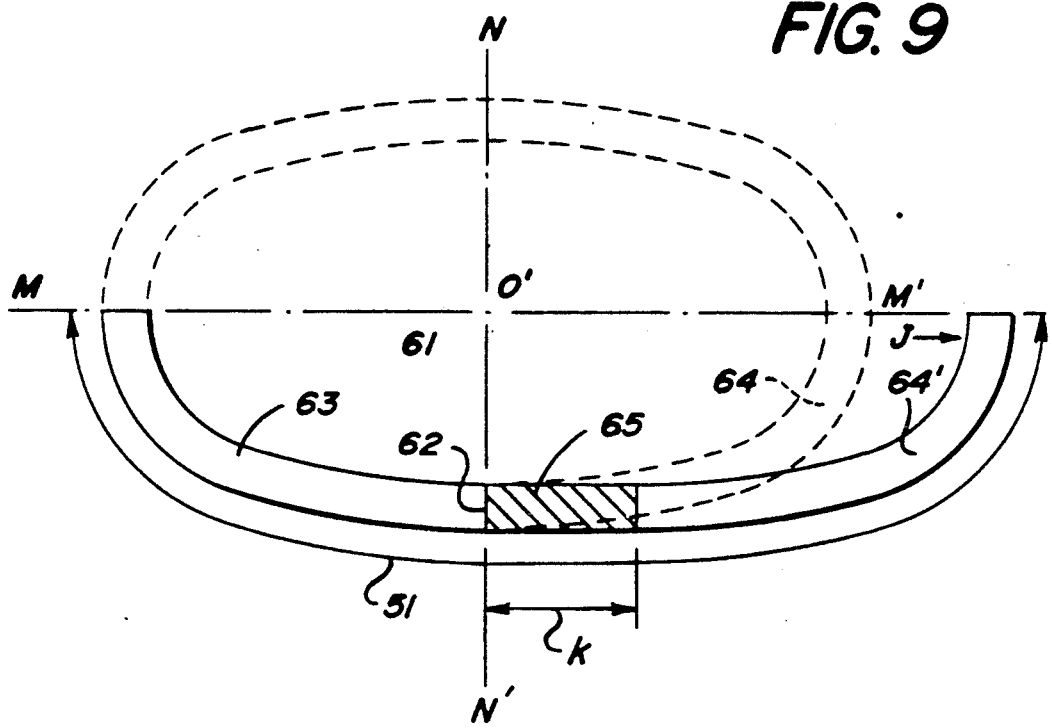
FIG. 9 is a view of the layout of the design of the lower portion of the rib of FIG. 7.

Upper portion 50 of flat oval 49 is laid out, as shown in FIG. 8, in solid lines as the top half of ellipse 60, which has a major axis X-X' of about 25 inches and a minor axis Y-Y' of about 16 inches, about two thirds the length of axis X-X'. Axes X-X' and Y-Y' intersect at 0. Lower portion 51 of flat oval 49, is laid out, as shown in FIG. 9, as the lower half of ellipse 61 which has a major axis M-M' of about 19 inches and a minor axis N-N' of about 11¼ inches. Axes M-M' and N-N' intersect at O'. The lower half of ellipse 61 is split at its midpoint 62 on the N-N' axis into quarters 63 and 64, shown in phantom, and separated by moving quarter 64' a distance k of about 6 inches in the direction indicated by arrow J. Straight extension 65 is laid out in the space between sections 63 and 64' to form with such sections the elongated half ellipse shape 51 shown in solid lines in the lower portion of flattened oval 49 of FIG. 7.

Laid out in the manner described above, as shown in FIG. 7, flattened oval 49 has a major axis X-O-X' of about 25 inches and a minor axis YO-O'N' of about 13⅝ inches, i.e. about 8 inches for the distance YO and about 5⅝ inches for the distance O'N', which is slightly larger than one-half the length of the major axis. With rib height H of about 2 inches, oval 49 has an outer perimeter or circumference, i.e. the distance along rib top 41, of about 62 inches and an inner circumference, i.e. the distance along rib bottom 42, of about 53 inches. Flattened oval 49 is symmetrical about its minor axis YO-O'N' and non-symmetrical about its major axis X-O-X'. After the pattern of rib 40 is laid out on sheet material 48, the rib 40 is cut from material 48 and then cut at the midpoint of the bottom elongated half ellipse at double line 43–44, which become the ends of rib 40. The other ribs 40 required for cover sections 4A, 4B and 4C are laid out and cut in similar fashion. Obviously, the flattened oval shape 49 of ribs 40 cannot easily be stretched or extended in a flat manner to the arch-like shape shown schematically in FIG. 6. However, this is somewhat the shape the ribs 40 assume when fastened into cover sections 4A, 4B and 4C in the manner hereinafter described and the arch-like shape which the ribs 40 assume when such cover sections are inflated.

As shown in FIGS. 3, 4, 5, 6 and 10, cover section 4A is assembled by fastening, in a spaced relationship, the bottoms 42 of seven ribs 40 to the top side 31 of bottom sheet 30 and by fastening, in a spaced relationship, the tops 41 of ribs 40 to the underside 22 of top sheet 20 in the following manner. The perimeter along the length of top 41 of each rib 40 is about 62 inches in length, which is about eight inches shorter than the 70-inch length b of top sheet 20. The perimeter along the length of bottom 42 of each rib 40 is about 53 inches, which is about 17 inches shorter than the 70-inch length d of bottom sheet 30.

A first rib 40 is centered on the top side 31 of bottom sheet 30, extending longitudinally thereof adjacent side 36, i.e. about one-half inch from such side, leaving sheet end portions 37 and 38, respectively, which extend between a central portion, unmarked, extending about 8½ inches beyond each of rib ends 43 and 44 respectively. With rib 40 centered on the top side 31 of bottom sheet 30, rib bottom 42 is fastened first adjacent rib end 43 to sheet top side 31, about 8½ inches from bottom sheet front edge 33, and then adjacent side 36 along seam 39 extending longitudinally of bottom sheet 30 for the full length of rib bottom 42 to rib end 44, ending about 8½ inches from bottom sheet back edge 34. A second rib bottom 42 is fastened to top side 31 of bottom sheet 30, along seam 39 adjacent side 35, i.e. about one-half inch from such side, extending longitudinally of bottom sheet 30 for the full length of second rib bottom 42 in the same manner as the first rib. The remaining five ribs 40 of cover section 4A are fastened along seams 39, generally parallel to the seams of the first two ribs and equidistant apart, i.e. about 4 inches. In fastening the bottoms 42 of ribs 40 to the top side 31 of bottom sheet 30, it may be necessary to slightly tuck or gather a rib bottom 42 to facilitate its fastening to the bottom sheet. This is particularly true, as shown in FIG. 3, adjacent the areas where rib upper portion 45 merges with leg portions 46 and 47, respectively.

After the bottoms 42 of the seven ribs 40 are fastened along seams 39 to the top side 31 of bottom sheet 30, top sheet 20 is centered above ribs 40 and the top 41 of each rib 40 is fastened to the underside 22 of top sheet 20, along a longitudinally extending seam 27. One rib top 41 is fastened along a seam 27 adjacent side 26 of top piece 20, above seam 39 of rib bottom 42. The top 41 of the remaining six ribs 40 are fastened equidistant apart, i.e.

about 4 inches, along seams 27, above seams 39 of rib bottoms 42, between top sheet sides 26 and 25, respectively, progressing first from the rib adjacent top sheet side 26 then sequentially toward top sheet side 25. The rib tops 41 are fastened in a manner somewhat similar to that used to fasten the rib bottoms 42 to topside 31 of bottom sheet 30.

Figure 10:
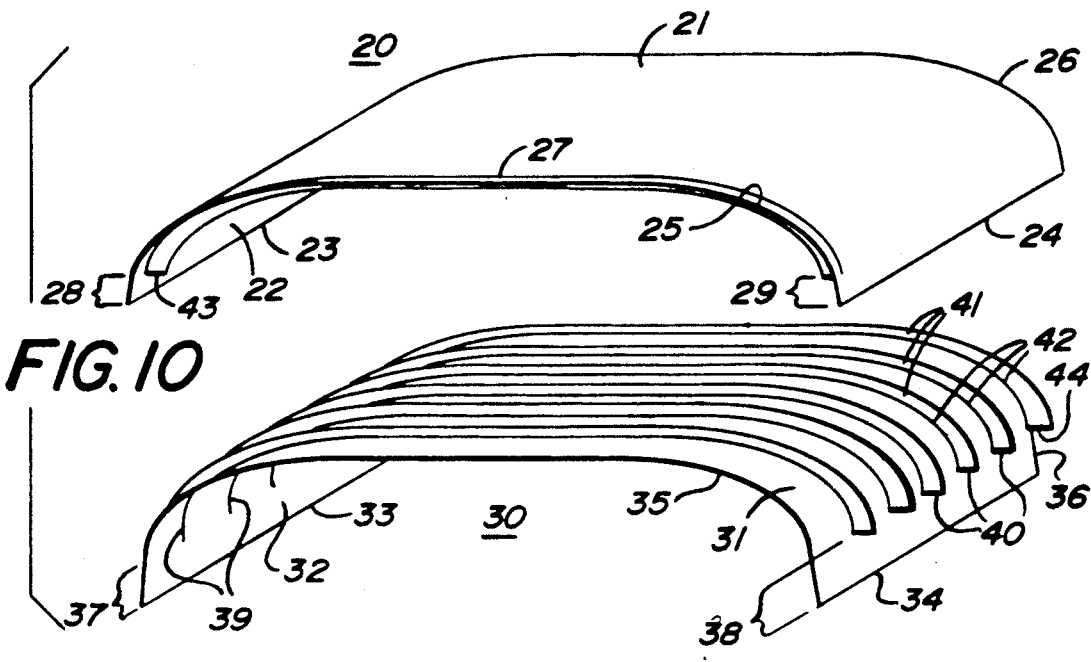
FIG. 10 is a view showing the partial assembly of the parts of one section of the cover of this invention.

As shown in FIGS. 3, 4 and 10, top sheet end portions 28 and 29, respectively, extend about four inches beyond each of rib ends 43 and 44, respectively, which is about one half the 8½ inches that bottom sheet end portions 37 and 38 extend beyond rib ends 43 and 44, respectively. Top sheet 20, adjacent front edge 23, is fastened adjacent front edge 33 of bottom sheet 30 to form air duct 11. Top sheet 20 adjacent back edge 24 is fastened adjacent back edge 34 of bottom sheet 30 to form air duct 12.

Cover sections 4B and 4C have parts identical to those of cover section 4A and are formed in the same manner. As best shown in FIG. 2, air ducts 11 and 12 of section 4A each have a closing tab slide fastener section 80 at one end and an engaging slide fastener section 81 at the opposite end. Air ducts 11 and 12 of sections 4B and 4C are fitted in an identical manner with slide fastener sections 80 and 81, respectively. The slide fastener sections 80 and 81, respectively, and cover section fasteners 8 permit sections 4A, 4B and 4C easily to be joined or separated. Closing tab slide fastener sections 81 at the ends of ducts 11 and 12, respectively, of cover section 4A engage slide fastener sections 80 at adjacent ends of ducts 11 and 12, respectively, of cover section 4B and connect ducts 11 of sections 4A and 4B and ducts 12 of sections 4A and 4B. In similar fashion, closing tab slide fastener sections 81 at the ends of ducts 11 and 12, respectively, of cover section 4B engage slide fastener sections 80 at adjacent ends of ducts 11 and 12, respectively, of cover section 4C and connect ducts 11 of sections 4B and 4C and ducts 12 of sections 4B and 4C. Ducts 11 and 12, respectively, of section 4C are closed at their outer ends, i.e. the ends opposite section 4B, by caps 82, which include a closing tab slide fastener section, unnumbered, to engage the slide fastener sections 81 at the ends of ducts 11 and 12, respectively, of section 4C. Duct 12 of section 4A is closed at its outer end, i.e. the end opposite section 4B, by cap 83, which includes a slide fastener, unnumbered, to engage the closing tab slide fastener section 80 at the outer end of duct 12. Air delivery tube 6 connects with the outer end, i.e. the end opposite section 4B, of air duct 11 of section 4A by means of slide fastener section 81 which engages closing tab slide fastener section 80 at the outer end of duct 11.

As shown in FIGS. 1 and 4, to inflate cover 4, pressurized air from blower 5 passes through tube 6 to duct 11 of section 4A and then to sections 4B and 4C. The pressurized air passes to Section 4A in the direction of arrow R and through duct 11 where it is partially diverted. A portion of the air from duct 11 flows in the direction of arrows S through compartments 70 of section 4A to duct 12, and a portion of the air continues through duct 11 of section 4A to duct 11 of section 4B. The air passing to section 4B acts in a similar fashion. A part of the air passing to duct 11 of section 4B flows through compartments 70 to duct 12 and a portion continues through duct 11 of section 4B to duct 11 of section 4C. The air passing to duct 11 of section 4C flows through compartments 70 of section 4C to duct 12. End caps 82 on the outer ends of ducts 11 and 12 of section 4C and end cap 83 at the outer end of duct 12 of section 4A prevent the escape of any significant portion of pressurized air from sections 4A and 4C.

Air fed from blower 5 through tube 6 to air ducts 11 of sections 4A, 4B and 4C causes their support portions 10 to inflate and assume an arch-like shape best illustrated in FIGS. 3 and 4. The arch-like shape of each cover support portion 10 comprises central portion 17 and depending, outwardly extending leg portions 18 and 19, which are slightly bowed or curved. The arch-like shape results from the as-cut, generally flattened oval shape of ribs 40 which are fastened to bottom sheet 30 and top sheet 20 in the spaced manner described. It is thought that when cover 4 is inflated the as-cut, generally flattened oval shape of the ribs and their spacing restrains or prestresses bottom sheet 30 and top sheet 20 to cause cover portion 10 to assume the described self-supporting arch-like shape. Air ducts 11 and 12 at opposite lower ends of cover portion 10 of each of sections 4A, 4B and 4C further raise the sections to provide a clearance G of about 14 inches between the underside 32 of bottom sheet 30 and the top of mattress 2. Generally, the width W of inflated cover 4 is about 34 inches, slightly less than the width Z of 36 inches of mattress 2. However, because of the flexibility of the materials of which cover 4 is made, depending, outwardly extending leg portions 18 and 19, respectively, easily can be moved either inwardly or outwardly to create a larger or smaller span or width. Moving the leg portions inwardly raises the height of the cover, and moving them outwardly lowers the height of the cover above the mattress.

The double air ducts, i.e. 11 and 12, respectively, at opposite lower ends of cover support portion 10, permit pressurized air to be fed to cover 10 through either air duct 11 or 12, or through both ducts. By forming cover 4 with three sections 4A, 4B and 4C, which are joined adjacent their sides as described above, and by having air fed to ducts 11 in series from one section to another along one side of said sections, one or more of the sections may be raised individually to provide access to selected portions of a patient's body for treatment purposes. When the appropriate fasteners 8 of the section to be raised are released along with the appropriate slide fastener sections 80 or 81, as the case may be, the open end or ends of duct or ducts 12 of an adjacent section or sections may be closed by an appropriate duct closure 82 or 83. If this is done rapidly and carefully, the end with duct 12 of the isolated section may then be raised by virtue of the lightweight and flexibility of the materials of the section, without causing one or more of the other sections to deflate, since pressurized air continues to flow through ducts 11 and compartments 70 of each section. If desired, air tube 6 easily can be switched from the outer end of duct 11 of section 4A to duct 12 at the opposite end of section 4A, and the end of duct 11 may be closed so that access can be had to the other side of patient 1 for treatment purposes.

The preferred embodiment of cover 4 described above is formed of three sections 4A, 4B and 4C, each with seven ribs 40, forming six compartments 70 and having two air ducts 11 and 12, respectively, at opposite ends of each section. However, the cover may be formed as a single unit, or with as many sections as reasonably desired, and the number of ribs may be changed in similar fashion. The cover and its sections may be formed with a single air duct extending longitudinally of one side of the cover or positioned at any other convenient location. For example, a single air duct may extend longitudinally of the cover, along the cover top sheet 20 with appropriate openings on the top sheet to permit air to flow from the duct to the compartments 70.

ALTERNATIVE EMBODIMENT

The preferred embodiment of the cover invention described above is suitable as a protective enclosure for placement over hospital patients, for example, whose treatment requires minimal or, preferably, no direct contact of any materials with the patient's skin. In many cases, it is desirable to control the environment about such a patient by regulating the temperature and/or the humidity of the air circulating about such patient. For this purpose, an alternative embodiment of the present invention is described. It will be observed in the alternative embodiment of FIGS. 6 and 11-14, that where common reference numerals are applicable, the same have been employed.

The alternative embodiment of the inflatable, self-supporting cover of the present invention shown in FIGS. 6, 11-14 is directed primarily to the provision of a supplemental sheet 90, which is fastened at spaced intervals to the underside 32 of bottom sheet 30 of cover section 4'A. As best shown in FIG. 6, supplemental sheet 90 has top side 91, underside 92, front edge 93, back edge 94, central portion, unmarked, and sides 95 and 96. Supplemental sheet 90 has a length f of about 70 inches, which is about the same length as b and d of top and bottom sheets 20 and 30, respectively. Supplemental sheet 90 has a width g of about 31 inches, which is about 6 inches wider than the 25-inch width c and e of top and bottom sheets 20 and 30, respectively.

In assemblying the alternative embodiment of the invention in a cover of three sections, the assembly being shown for one section 4'A in FIGS. 11-14, cover bottom sheet 30 is positioned centrally on top of supplemental sheet 90, with bottom sheet underside 32 against supplemental sheet top side 91 and with bottom sheet front edge 33 adjacent supplemental sheet front edge 93 and bottom sheet back edge 34 adjacent supplemental sheet back edge 94. Supplemental sheet 90 has a central portion, unmarked, and end portions 97 and 98, respectively, comparable to bottom sheet central portion and end portion 37 and 38. In a flat position, supplemental sheet side 95 extends a distance h of 3 inches beyond bottom sheet side 35, and supplemental sheet side 96 extends a distance i of 3 inches beyond bottom sheet side 36.

As shown in FIGS. 6, 12 and 13, starting 8½ inches from front edges 93 and 33, respectively, of supplemental sheet 90 and bottom sheet 30, the two sheets are fastened together along a first common seam 100, which is spaced about one-half inch from their sides 96 and 36, respectively, and extends generally parallel to them. Common seam 100 extends longitudinally, i.e. along the length, of sheets 90 and 30, respectively, to a point 8½ inches from their back edges 94 and 34, respectively. Common seam 100 does not extend through bottom sheet end portions 37 and 38, respectively, and supplemental sheet end portions 97 and 98, respectively. Sheets 90 and 30, respectively, are fastened together along a second common seam 100, which extends generally parallel to first seam 100. Second common seam 100 on bottom sheet 30 is spaced four inches from first seam 100 and on supplemental sheet 90 the second common seam 100 is spaced five inches from first seam 100, one inch farther apart than on bottom sheet 30. Sheets 90 and 30, respectively, are fastened together along five other generally parallel common seams 100, which are spaced apart a distance of four inches on bottom sheet 30 and five inches on supplemental sheet 90. The last such common seam 100 is spaced about one-half inch from sides 95 and 35, respectively, of supplemental sheet 90 and bottom sheet 30 and extends longitudinally of such sheets and generally parallel to such sides. In supplemental sheet 90, midway between the common seams 100 and for about their length, are a plurality of ports 101 which are about one-quarter inch in diameter and spaced about one inch apart.

Figure 11:
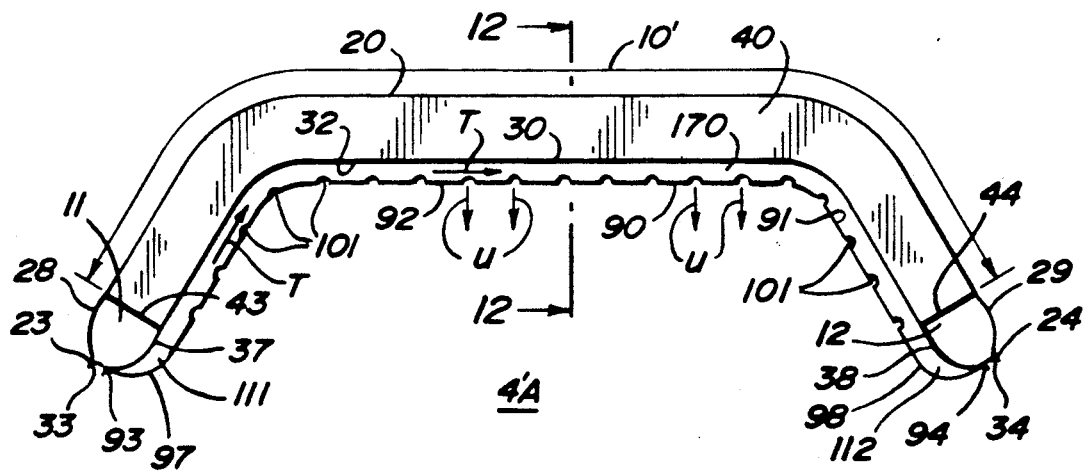
FIG. 11 is an end view partly in section, of another embodiment of a cover section of this invention.

After bottom sheet 30 and supplemental sheet 90 are fastened together along seams 100, the remainder of cover section 4'A is assembled in the manner described with respect to the preferred embodiment. That is, ribs 40 are fastened to bottom sheet 30 and top sheet 20 to form cover support portion 10 and, air ducts 11 and 12, respectively, are formed by joining the front edges 23 and 33, respectively, and back edges 24 and 34 respectively, of top sheet 20 and bottom sheet 30. Then, as shown in FIGS. 11 and 14, supplemental sheet front edge 93 is fastened to bottom sheet end portion 37 adjacent bottom sheet front edge 33 thereby forming between bottom sheet end portion 37 and supplemental sheet end portion 97 supplemental air duct 111. In similar fashion, supplemental sheet back edge 94 is fastened to bottom sheet end portion 38 adjacent bottom sheet back edge 34 thereby forming between bottom sheet end portion 38 and supplemental sheet end portion 98 supplemental air duct 112. Cover sections 4'B and 4'C, not shown, are assembled in a similar fashion.

Sections 4'A, 4'B and 4'C, the latter two not shown, are fitted with appropriate slide fasteners 120, not shown, and their respective air ducts 111 and 112 are connected by slide fasteners, not shown, designed in the shape of slide fasteners 120 shown in FIG. 14, all in a fashion similar to the slide fasteners of section 4A, 4B and 4C. The design of zipper sections 120 conform to the construction of double ducts 11 and 111 and 12 and 112. As required, open ends of ducts 111 and 112 of such cover sections are closed by appropriate air duct closures 122 and 123, not shown, which are designed in the configuration of slide fastener 120. In similar fashion, the end of air delivery tube 6 is fitted with an appropriate slide fastener to engage the slide fastener 120 at the end of ducts 11 and 111 of section 4'A.

Cover sections 4'A and 4'B and 4'C, the latter two not shown, are inflated in the same manner as described above for the preferred embodiment of the covers 4, except that air from blower 5 and air delivery tube 6 passes to both air duct 11 and air duct 111. Air from duct 11 inflates cover support portion 10', i.e. the upper portion of cover section 4'A. From air duct 11, the air flows also into compartments 170, i.e. the lower portion of cover section 4'A, which are formed by the sagging manner in which supplemental sheet 90 is fastened along seams 100 to bottom sheet 30. The sagging results from the 5-inch distance between seams 100 of supplemental sheet 90 which are fastened to bottom sheet 30 along common seams 100 that are spaced at 4-inch intervals. Cover section 4'A forms with cover sections 4'B and 4'C, not shown, cover 4', not shown. Air flowing into compartments 170 of such sections exits through ports 101 in the direction shown by arrow u and circulates about a patient beneath such cover.

The term "flattened oval" as used herein refers to a composite figure which, as laid out in FIGS. 7, 8 and 9, includes the top half of a first oval and the bottom half of a second, smaller oval that is stretched or extended at its vertical mid-point to give the smaller oval a flattened appearance. The first oval has a major axis and a minor axis, which is about 65% percent the length of the major axis. The second, smaller oval has a major axis, which has a length about 75% of the length of the first oval major axis, and a minor axis, which has a length about 70% of the length of the first oval minor axis and about 60% of the length of the second oval major axis. The second oval is stretched or extended at its major axis to form a flattened portion which gives the second oval a flattened shape. The extended second oval has a major axis length about equal to that of the first oval major axis. While the shape of the ovals laid out in FIGS. 7, 8 and 9 are in the form of an ellipse, the ovals may be laid out in the form of a parabola, hyperbola or cycloid.

For a hospital bed with a mattress width of about 36 inches, ribs 40 are laid out with a top length or perimeter of about 62 inches, but the length may reasonably vary between about 57 inches to 67 inches. The rib height H of about two inches permits an overlap at its top and bottom of about $\frac{1}{8}$th to $\frac{1}{4}$ inch where the ribs are fastened along seams 27 and 39 to top and bottom sheets 20 and 30, respectively. The rib overlap results in a distance of between one-and-a-half to one-and-three-quarter inches between the underside 22 of top sheet 20 and top side 31 of bottom sheet 30. However, the rib height H may vary between about $1\frac{1}{4}$ to 3 inches. The spacing of ribs 40 in cover support portion 10 is preferably about four inches, but the spacing may vary between about three to six inches. Varying one or more of the dimensions of the ribs of the preferred embodiment of cover 4 will obviously change its appearance, either thin or thick, generally flat or bulging and vary the distance between the underside of the cover and the top of a mattress upon which the cover ends or ducts rest. The number of sections may vary in a similar manner. The tops 41 and bottoms 42 of ribs 40 are fastened to the underside 22 of top sheet 20 and the top side 31 of bottom sheet 30 along seams 27 and 39, respectively, by sewing, although the fastening can be accomplished by a suitable adhesive, heat sealing and/or closely spaced staples.

In the alternative embodiment of the invention, ducts 170 extend transversely of the length of cover section 4'A and of mattress 2 in the same manner as do ducts 70 of cover support portion 10'. In a further embodiment, ducts 170 may extend longitudinally of the length of cover section 4'A and of mattress 2, with an appropriately portioned air duct.

In the event the cover of this invention is to be used to span a width greater than about 36 inches, e.g. a wider bed, the above mentioned dimensions must be proportionately modified. Inflation of cover 4 formed of sections 4A, 4B and 4C, as described above, requires a blower with an air capacity of about one cubic foot per second. There is some leakage of air from cover 4, particularly where ducts 11 and 12 of one section connect with those of another section or at the capped ends of certain ducts. There is also some leakage of air through the holes created by the sewing of the tops and bottoms of ribs 40 along seams 27 and 39, respectively. For a cover of the alternative embodiment, i.e. with a bottom portion formed of supplemental sheet 90 with its plurality of ports 101, a larger blower capacity may be required or an additional blower may be required. With two blowers one blower feeds ducts 11 of the upper cover portion and one blower feeds ducts 111 of the cover lower portion. In certain instances, it is desirable to control the temperature and/or humidity of the air being circulated about a patient and in such an instance, temperature and humidity control apparatus may be connected between the blowers and the air delivery tube 6.

The material of the preferred embodiment of cover 4 of this invention should be lightweight, durable, non-permeable, and asthetically pleasing. The preferred material is spun-bonded olefin formed from high density polyethylene fibers manufactured by a continuous process in which fine, non-directional fibers are spun and bonded together by heat and pressure. Dupont Tyvek ®, style 1422A, is such a non-permeable material. The alternative embodiment of the invention may also be made totally of Tyvek ®, style 1422A. However, it is possible to form the alternative embodiment with supplemental sheet 90 formed of a permeable material so that no separate ports 101 are necessary. Such a permeable material is Dupont Tyvek ®, style 1622E, which is a spun-bounded olefin perforated with 10–15 mil. (0.25–38 mm) holes, which provide air and moisture permeability and additional softness and flexibility.

Although particular embodiments of the invention have been shown and described in full herein, there is no intention to thereby limit the invention to the details of such embodiments. On the contrary, the intention is to cover all modifications as fall within the spirit and scope of the invention, specification and the appended claims.

The number, size and spacing of ports 101 may be varied to satisy the requirements for air distribution in and about a patient. The ports may be round, elongated slots or any other desirable shape. While pressurized air has been referred to with respect to the above described cover, any safe gaseous medium may be used to inflate the cover and/or circulate about a patient beneath the cover. The temperature of the medium and its humidity may be controlled within desired ranges and medication can be added to treat the patient. The cover of this invention is free-standing, i.e. it may be rested on a base, such as a hospital bed, without any additional support.

We claim:
1. A free standing inflatable, open-ended, self-supporting cover suitable for placement, independent of any external support, over a body, comprising:
   (A) an inflatable cover support portion comprising:
      (a) a top sheet,
      (b) a bottom sheet, and
      (c) a plurality of spaced ribs formed by cutting the shape of a flattened oval from a single sheet of material extending transverse to the length of said cover between said top and bottom sheets and separating said cover support portion into a plurality of compartments; and
   (B) a duct connecting with said cover support portion compartments and having an opening therein for admitting pressurized gas thereto for circulation to and through said cover support portion compartments for inflation thereof, whereby said cover support portion assumes an arch-like shape transverse to said cover and spanning said body independent of any external support.

2. The cover of claim 1 wherein said inflatable cover support portion includes a central portion and first and second downwardly and outwardly extending leg portions at opposite ends of said central portion and each said rib includes an upper portion and first and second downwardly and outwardly extending leg portions at opposite ends of said rib upper portion.

3. The cover of claim 2 wherein said duct extends longitudinally of said cover adjacent the lower end of the first downwardly and outwardly extending leg portion of said cover support portion 4. A free standing, inflatable, open-ended, self-supporting cover suitable for placement, independent of any external support, over a body, comprising:
   (A) an inflatable cover support portion comprising:
       (a) a top sheet,
       (b) a bottom sheet, and
       (c) a plurality of spaced ribs, formed by cutting the shape of a flattened oval from a single sheet of material and fastened transversely to the length of said cover between said top and bottom sheets and separating said cover support portion into a plurality of compartments; and
   (B) a duct connecting with said cover support portion compartments and having an opening therein for admitting pressurized gas thereto for circulation to and through said cover support portion compartments for inflation thereof, whereby said cover support portion assumes an arch-like shape transverse to said cover and spanning said body, independent of any external support.

5. The cover of claim 4 wherein each said rib is formed in the shape of a flattened oval symmetrical about the minor axis thereof and non-symmetrical about the major axis thereof.

6. The cover of claim 4 wherein the rib shape of the flattened oval comprises a composite figure having an upper portion in the shape of the upper half of a first oval having a major axis and a minor axis and a bottom portion in the shape of the bottom half of a second, smaller oval having a minor axis smaller than the minor axis of the first oval and a major axis that is extended to the length of the major axis of the first oval.

7. The cover of claim 6 wherein the outer periphery of the flattened oval rib shape is between about 57 to 67 inches.

8. A free-standing, inflatable, open-ended, self-supporting cover suitable for placement, independent of any external support, over a body, comprising:
   (A) at least two inflatable cover support portions, each comprising:
       (a) a top sheet,
       (b) a bottom sheet,
       (c) a plurality of spaced ribs formed in the shape of a flattened oval and fastened transversely to said cover between said top and bottom sheets and separating each said cover support portion into a plurality of compartments, extending transverse to said cover; and
   (B) a duct connecting with the compartments of each said cover support portion and having an opening therein for admitting pressurized gas thereto for circulation to and through the compartments of each said cover support portion for inflation thereof, whereby each said cover support portion assumes an arch-like shape transverse to said cover and spanning said body, independent of any external support.

9. The cover of claim 8 wherein each inflatable cover support portion includes a central portion and first and second downwardly and outwardly extending leg portions at opposite ends of the central portion and each said rib includes an upper portion and first and second downwardly and outwardly extending leg portions at opposite ends of the upper portion.

10. The cover of claim 9 wherein the duct extends longitudinally of said cover adjacent the lower end of the first downwardly and outwardly extending leg portion of said cover support portions.

11. A free-standing, inflatable, open-ended, self-supporting cover suitable for placement, independent of any external support, over a body, comprising:
    (A) a first inflatable cover section having a width extending transverse to said cover, comprising:
       (a) a top sheet having:
           (i) a length extending longitudinally of the width of said cover section,
           (ii) a first-outer edge,
           (iii) a first end portion extending inwardly from the first outer edge and having a first inner end, and
           (iv) a central portion connecting with the first inner end of the first end portion;
       (b) a bottom sheet having:
           (i) a length extending longitudinally of the width of said cover section,
           (ii) a first outer edge,
           (iii) a first-end portion extending inwardly from the first outer edge and having a first inner end, and
           (iv) a central portion connecting with the first inner end of the first-end portion;
       (c) a plurality of spaced ribs formed in the shape of a flattened oval and fastened longitudinally of a portion of the length of said top and bottom sheets and separating said first cover section into a plurality of compartments; and
       (d) a duct, extending longitudinally of said first cover section and connecting with each compartment thereof, formed by fastening the first end portion of said top sheet, adjacent the first outer edge thereof, to the first end portion of said bottom sheet, adjacent the first outer edge thereof, and having an end for connection with a source of pressurized gas for circulation to and through said duct and the compartments for inflation of said first cover section whereby said first cover section assumes an arch-like shape transverse to said cover and spanning said body, independent of any external support.

12. The cover of claim 11 further comprising:
    (A) a second inflatable cover section having a width extending transversely to said cover, comprising:
       (a) a to sheet having:
           (i) length extending longitudinally of the width of said cover section,
           (ii) a first outer edge,
           (iii) a first end portion extending inwardly from the first outer edge and having a first inner end, and
           (iv) a central portion connecting with the first inner end of the first end portion;
       (b) a bottom sheet having:
           (i) a length extending, longitudinally of the width of said cover section,
           (ii) a first outer edge, (iii) a first end portion extending inwardly from the first outer edge and having a first inner end, and (iv) a central portion connecting with the first inner end of the first end portion;

(c) a plurality of spaced ribs formed in the shape of a flattened oval and extending longitudinally of a portion of the length of said top and bottom sheets and separating said second cover section into a plurality of compartments; and (d) a duct extending longitudinally of said second cover section and connecting with each compartment thereof, formed by fastening the first end portion of said top sheet, adjacent the first outer edge thereof, to the first end portion of said bottom sheet, adjacent the first outer edge thereof, and connecting with an adjacent end of said first duct of said first cover section whereby pressurized gas from said first cover section first duct passes to said second cover section second duct and through the compartments thereof to cause said second cover section to assume an arch-like shape transverse to said cover and spanning said body, independent of any external support.

13. The cover of claim 11 wherein said first inflatable cover section includes a central portion and first and second downwardly and outwardly extending leg portions at opposite ends of said central portion and each rib includes an upper portion and first and second downwardly and outwardly extending leg portions at opposite ends of said rib upper portion.

14. The cover of claim 11 wherein each said rib is formed in the shape of a flattened oval symmetrical about the minor axis thereof and non-symmetrical about the major axis thereof.

15. The cover of claim 11 wherein the shape of the flattened oval comprises a composite figure having an upper portion in the shape of the upper half of a first oval having a major axis and a minor axis and a bottom portion in the shape of the bottom half of a second smaller oval having a minor axis smaller than the minor axis of the first oval and a major axis that is extended to the length of the major axis of the first oval.

16. The cover of claim 15 wherein each said rib has a height of between about one and one-quarter to three inches and has a top perimeter of between about fifty-seven to about sixty-seven inches.

17. A free-standing, inflatable, open-ended, self-supporting cover suitable for placement, independent of any external support, over a body, comprising:

(A) a first inflatable cover section comprising:
(a) a top sheet having:
(i) a length extending longitudinally of the length of said first inflatable cover section and a width extending transversely thereof,
(ii) a first outer edge and a second outer edge,
(iii) a first end portion extending inwardly from the first outer edge thereof and having a first inner end,
(iv) a second end portion extending inwardly from the second outer edge thereof and having a second inner end, and
(v) a middle portion extending between the inner end of the first end portion and the inner end of the second end portion;
(b) a bottom sheet having:
(i) a length extending longitudinally of the length of said first inflatable cover section and a width extending transversely thereof,
(ii) a first outer edge and a second outer edge,
(iii) a first end portion extending inwardly from the first outer edge thereof and having a first inner end,
(iv) a second end portion extending inwardly from the second outer edge thereof and having a second inner end, and
(v) a middle portion extending between the inner end of the first end portion and the inner end of the second end portion;

(c) a plurality of spaced ribs formed in the shape of a flattened oval and fastened to extend longitudinally of the width of said bottom sheet and separating said first inflatable cover section into a plurality of first compartments;

(d) a first duct extending longitudinally of said first inflatable cover section and formed by joining the first end portion of said top sheet, adjacent the first outer edge thereof, to the first end portion of said bottom sheet, adjacent the first outer edge thereof, connecting with each first compartment and having an end for connection with a source of pressurized gas for passage to and through the duct and first compartments for inflation of said first inflatable cover section whereby said first inflatable cover section assumes an arch-like shape transverse to said cover and spanning said body;

(e) a second duct extending longitudinally of said first inflatable cover section and formed by joining the second end portion of said top sheet, adjacent the second outer edge thereof, to the second end portion of said bottom sheet, adjacent the second outer edge thereof, and connecting with each first compartment.

18. A free-standing, inflatable, open-ended, self-supporting cover suitable for placement over a body and for circulating a pressurized gas thereabout, comprising:

(A) a top portion comprising a plurality of compartments extending transversely of the length of said cover;

(B) a bottom portion fastened to the underside of said top portion and comprising a plurality of compartments; and (C) a duct connecting with the top portion compartments and having an opening therein for admitting pressurized gas for passage therethrough and through said top portion compartments for inflation thereof, whereby said cover top portion assumes an arch-like shape transverse to said cover and spanning said body.

19. The cover of claim 18 wherein each of said bottom portion compartments includes at least one port and connects with said duct whereby pressurized gas from said duct also passes into and through said bottom portion compartments and out of said ports therein.

20. The cover of claim 18 further including a second duct connecting with said bottom portion compartments and having an opening for admitting pressurized gas for passage therethrough and through said bottom portion compartments and out of said ports therein.

21. A free-standing, inflatable, open-ended, self-supporting cover suitable for placement over a body and for circulating a pressurized gas thereabout, comprising:

(A) a top portion comprising:
  (a) a top sheet,
  (b) a bottom sheet,
  (c) a plurality of spaced ribs extending between the underside of said top sheet and top side of said bottom sheet forming a plurality of first compartments extending transversely of the length of said cover;

(B) a bottom portion fastened to the underside of said top portion bottom sheet and having a plurality of second compartments each having at least one port therein;

(C) a duct connecting with the top portion first compartments and having an opening therein for admitting pressurized gas for passage therethrough and through the top portion first compartments for inflation thereof whereby said cover top portion assumes an arch-like shape transverse of the length of said cover and spanning said body.

22. The cover of claim 21 wherein said duct also connects with the bottom portion second compartments for passage of pressurized gas from said first duct to said second compartments and from said ports therein.

23. A free-standing, inflatable, open-ended, self-supporting cover suitable for placement over a body and for circulating a pressurized gas thereabout, comprising:

(A) a top sheet,
(B) a bottom sheet,
(C) a plurality of spaced ribs extending between the underside of said top sheet and the top side of said bottom sheet and forming a plurality of first compartments extending transversely of the length of said cover;
(D) a supplemental sheet fastened to said bottom sheet along seams spaced apart a greater distance on said supplemental sheet than on said bottom sheet causing said supplemental sheet to sag between adjacent seams thereof and form at least one second compartment between the underside of said bottom sheet and the top side of said supplemental sheet,
(E) at least one port in said supplemental sheet between each pair of adjacent seams, and
(F) a first duct having an opening therein for connection with a source of pressurized gas, said duct connecting with the first compartments for the passage of pressurized gas therethrough for inflation thereof to cause said cover to assume an arch-like shape transverse to the length of said cover and spanning said body.

24. The cover of claim 23 further including a second duct spaced from said first duct and having an opening therein for connection with a source of pressurized gas, said second duct connecting with the first compartments.

25. The cover of claim 23 wherein said first duct also connects with the second compartments for the passage of pressurized gas therethrough and from said ports therein.

26. The cover of claim 23 further including a second duct spaced from said first duct and having an opening therein for connection with a source of pressurized gas for passage therethrough and through the second compartments and from said ports therein.

27. The cover of claim 23 wherein said supplemental sheet has a width greater than the width of said bottom sheet.

28. The cover of claim 23 wherein each said rib is formed in the shape of a flattened oval symmetrical about the minor axis thereof and non-symmetrical about a major axis thereof.

29. The cover of claim 23 wherein each said rib has a height between about one and one quarter to about three inches and a top perimeter of between about 57 inches to 67 inches.

30. A free-standing, inflatable, open-ended, self-supporting cover suitable for placement over a body and for circulating a pressurized gas thereabout, comprising:

(A) a first inflatable cover section extending transverse to the length of said cover, comprising:
  (a) a top sheet,
  (b) a bottom sheet,
  (c) a plurality of spaced ribs extending longitudinally of the width of said cover between said top and bottom sheets and separating said first cover section into a plurality of first compartments,
  (d) a supplemental sheet fastened to said bottom sheet along seams spaced apart a greater distance on said supplemental sheet than on said bottom sheet causing said supplemental sheet to sag between adjacent seams thereof and form at least one second compartment between the underside of said bottom sheet and the top side of said supplemental sheet,
  (e) at least one port in said supplemental sheet between each pair of adjacent seams, and
  (f) a first duct extending for about the length of said first cover section, having an end for connection with a source of pressurized gas for passage thereto and through said first compartments whereby said first cover section assumes an arch-like shape transverse to said cover and spanning said body;

(B) a second inflatable cover section extending transverse to the length of said cover, comprising:
  (a) a top sheet,
  (b) a bottom sheet,
  (c) a plurality of spaced ribs extending longitudinally of the width of said cover between said top and bottom sheets and separating said second cover section into a plurality of second compartments,
  (d) a supplemental sheet fastened to said bottom sheet along seams based apart a greater distance on said supplemental sheet than on said bottom sheet causing said supplemental sheet to sag between adjacent seams thereof and form at least one second compartment between said underside of said bottom sheet and the top side of said supplemental sheet,
  (e) at least one port in said supplemental sheet between each pair of adjacent seams, and
  (f) a second duct connecting with an adjacent end of said first duct of said first cover section whereby pressurized gas from said first cover section first duct passes to said cover section second duct and through each second compartment thereof to cause said second cover section to assume an arch-like shape transverse to said cover and spanning said body.

31. The cover of claim 30 wherein said first duct of said first cover section also connects with each second compartment thereof for admitting pressurized gas for passage therethrough and out of each said port therein and said second duct of said second cover section also connects with each second compartment thereof for admitting pressurized gas for passage therethrough and out of each said port therein.

32. The cover of claim 30 further including a third duct connecting with each second compartment of said first cover section and having an opening therein for admitting pressurized gas for passage therethrough and through each second compartment of said first cover section and out of each said port therein and a fourth duct connecting with said third duct and each second compartment of said second cover section for admitting pressurized gas for passage therethrough and through each second compartment of said second cover section and out of each said port therein.

33. The cover of claim 30 wherein said ribs of said first and second cover sections are formed in the shape of a flattened oval.

34. The cover of claim 30 wherein said ribs of said first and second cover sections are formed in the shape of a flattened oval symmetrical about the minor axis thereof and non-symmetrical about the major axis thereof.

35. The cover of claim 30 wherein said ribs of said first and second cover sections are formed in the shape of a flattened oval comprising a composite figure having an upper portion in the shape of the upper half of a first oval having a major axis and a minor axis and a bottom portion in the shape of the bottom half of a second, smaller oval having a minor axis smaller than the minor axis of the first oval and a major axis that is extended to the length of the major axis of the first oval.

36. The cover of claim 30 wherein the ribs of said first and second cover sections have a top length between about 57 to about 67 inches.

* * * * *